United States Patent
Lear et al.

(10) Patent No.: US 10,064,616 B2
(45) Date of Patent: Sep. 4, 2018

(54) VARIABLE STIFFNESS SUTURE BRIDGES COMPATIBLE WITH VARIOUS SUTURE PATTERNS

(71) Applicants: William Lear, Corvallis, OR (US); Jennifer Akeroyd, Corvallis, OR (US)

(72) Inventors: William Lear, Corvallis, OR (US); Jennifer Akeroyd, Corvallis, OR (US)

(*) Notice: Subject to any disclaimer, the term of this patent is extended or adjusted under 35 U.S.C. 154(b) by 0 days.

(21) Appl. No.: 15/360,594

(22) Filed: Nov. 23, 2016

(65) Prior Publication Data
US 2017/0071596 A1  Mar. 16, 2017

Related U.S. Application Data

(63) Continuation-in-part of application No. 14/990,715, filed on Jan. 7, 2016.

(60) Provisional application No. 62/221,410, filed on Sep. 21, 2015, provisional application No. 62/193,764, filed on Jul. 17, 2015.

(51) Int. Cl.
*A61B 17/04* (2006.01)
*A61B 17/08* (2006.01)

(52) U.S. Cl.
CPC .......... *A61B 17/0466* (2013.01); *A61B 17/08* (2013.01); *A61B 2017/0495* (2013.01); *A61B 2017/081* (2013.01)

(58) Field of Classification Search
CPC ... A61B 17/0487; A61B 17/06; A61B 17/122; A61B 2017/0464; A61B 2017/045; A61B 2017/0454; A61B 17/0466; A61B 17/06061; A61B 2017/0496; A61B 2017/0495; A61B 2017/0406; A61B 2017/081

See application file for complete search history.

(56) References Cited

U.S. PATENT DOCUMENTS

| | | | | |
|---|---|---|---|---|
| 3,789,851 A * | 2/1974 | LeVeen | ............ | A61B 17/0466 606/148 |
| 3,831,608 A * | 8/1974 | Kletschka | .......... | A61B 17/0466 606/233 |
| 3,931,821 A * | 1/1976 | Kletschka | .......... | A61B 17/0466 24/129 R |
| 3,934,592 A * | 1/1976 | Wolvek | ............. | A61B 17/0466 606/233 |
| 4,275,736 A * | 6/1981 | Chodorow | ......... | A61B 17/0466 606/233 |
| 4,667,675 A * | 5/1987 | Davis | ................. | A61B 17/0466 24/71.1 |

(Continued)

*Primary Examiner* — Christopher L Templeton
(74) *Attorney, Agent, or Firm* — Wei & Sieman LLP

(57) ABSTRACT

A suture bridge to accommodate many common types of sutures, including a first leg and a second leg, where first leg and second leg include a patient contacting surface configured to contact a patient's skin. A first support connects to the first leg and second support connects to the second leg. A traversing member connects to the first support and the second support, and the first support and the second support elevate the traversing member away from the patient contacting surfaces of the first leg and the second leg creating a wound eversion void below the traversing member. This forms a wound eversion void which is a void configured to accept an everting wound. In some examples, the suture bridge includes notches on the first leg and the second leg to accommodate more types of sutures.

2 Claims, 5 Drawing Sheets

(56) References Cited

U.S. PATENT DOCUMENTS

| | | | | |
|---|---|---|---|---|
| 4,773,421 A | * | 9/1988 | Davis | A61B 17/0466 24/71.1 |
| 2001/0029381 A1 | * | 10/2001 | Bowman | A61B 17/0401 606/151 |
| 2008/0033487 A1 | * | 2/2008 | Schwartz | A61B 17/0401 606/232 |
| 2014/0222070 A1 | * | 8/2014 | Belson | A61B 17/08 606/216 |

* cited by examiner

VARIABLE STIFFNESS SUTURE BRIDGES COMPATIBLE WITH VARIOUS SUTURE PATTERNS

CROSS REFERENCE TO RELATED APPLICATIONS

This application is a continuation-in-part of U.S. patent application Ser. No. 14/990,715, filed on Jan. 7, 2016, which a non-provisional of and claims priority to U.S. Provisional Application No. 62/221,410, filed Sep. 21, 2015, and U.S. Provisional Application No. 62/193,764, filed Jul. 17, 2015, and this application is a non-provisional of and claims priority to U.S. Provisional Application No. 62/221,410, filed Sep. 21, 2015, and U.S. Provisional Application No. 62/193,764, filed Jul. 17, 2015, each of which is incorporated by reference in its entirety. Any and all applications for which a foreign or domestic priority claim is identified in the Application Data Sheet as filed with the present application are hereby incorporated by reference under 37 C.F.R § 1.57.

BACKGROUND

The present disclosure relates generally to devices for interfacing with medical sutures. In particular, suture bridges that elevate an external portion of a suture above a patient's skin to extend the useful life of the suture and to compress a wound are described.

Sutures are stitches used to close wounds and surgical incisions of a patient. A medical practitioner generally uses a needle with an attached thread to substantially sew two adjacent sections of skin together to close the wound or incision. Surgical knots are often used to secure the sutures and ensure proper healing. It the sutures are not implemented correctly, or the wound is not properly closed, the patient may be at risk of infection or improper healing of the wound. In addition, sutures and surgical knots contacting the skin can be inflammatory or become "ingrown" and actually impede healing of the wound or incision. Further, eversion of the wound or incision edges is a desirable feature of a would closure.

Known suture devices and implemented techniques for sutures are not entirely satisfactory for the range of applications in which they are employed. For example, exerting the edges of a wound currently is an operator skill requiring hours of training and practice and not always achievable. In addition, conventional suture devices are not employable with multiple types of suture techniques. Also, some conventional suture devices do not compress the wound to encourage proper healing and wound eversion. Thus, there exists a need for suture devices that improve upon and advance the design of known suture devices.

SUMMARY

The present disclosure is directed to suture bridges with a first leg and a second leg, where the first leg and second leg include a patient contacting surface configured to contact a patient's skin. A first support connects to the first leg and a second support connects to the second leg. A traversing member connects to the first support and the second support, and the first support and the second support elevate the traversing member away from the patient contacting surfaces of the first leg and the second leg to define a wound eversion void below the traversing member. The wound eversion void is configured to accept an everting wound.

Further, the patient contacting surface of the first leg is configured to contact a patient's skin on one side of a patient's wound, and the patient contacting surface of the second leg is configured to simultaneously contact a patient's skin on the opposite side of the patient's wound. The traversing member is configured to be over the patient's wound such that the wound eversion void can accept a patient's everting wound. This allows for a wound to evert when compressed by a suture, supported by the suture bridge, encouraging proper healing of the wound.

The first leg and second leg may be flexible to allow for patient comfort and reduce skin irritation. Additionally, the traversing member may be to keep the suture bridge from collapsing from the forces of the suture. To make the legs flexible and the traversing member rigid, the traversing member may be thicker, as measured from a top surface to a bottom surface, than the first leg and second leg as measured from the top surface to the bottom surface.

In some examples, there is a first inflection point where the first support connects to the first leg, and the first support and first leg form an obtuse angle. Similarly, there is a second inflection point where the second support connects to the second leg wherein the second support and the second leg form an obtuse angle. The first inflection point and the second inflection point are configured to accept and hold a suture thread. This allows for a horizontal mattress suture to be used with the suture bridge.

There is also a ridge and a groove on the top surface of the traversing member. The ridge serves to add extra support to the traversing member, and the ridge and groove both serve to accept and hold a suture thread.

There is a first hole extending through the first leg, and a second hole extending through the second leg. Additionally, a tab extends from a side of the second leg. The tab also has a hole extending through it. Both the first hole and the second hole, as well as the hole in the tab, allow for a suture thread to pass through them to accommodate the use of multiple common types of sutures.

In alternative examples, the suture bridge includes a first notch on an end of the first leg, and a second notch on the end of the second leg. These notches allow for even more types of sutures to be used with the suture bridge, including a vertical mattress suture.

DETAILED DESCRIPTION

Figure 1:
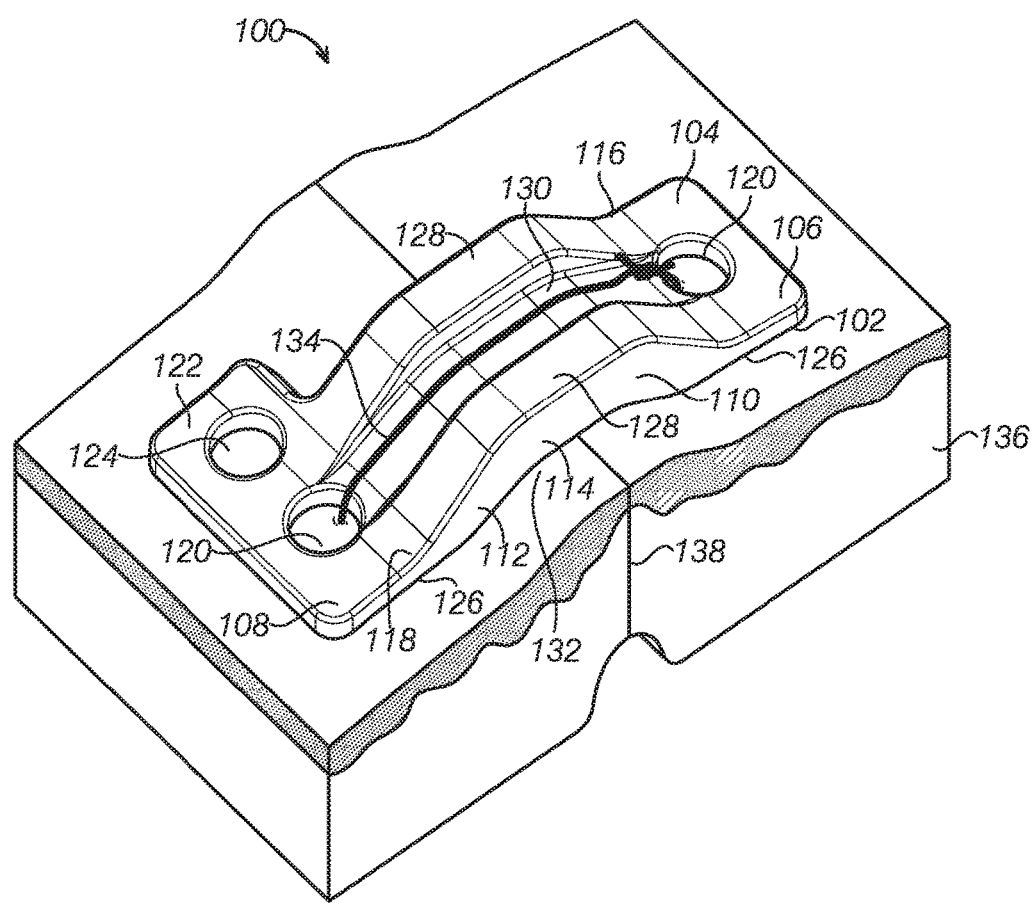
FIG. 1 is a perspective view of a first example of a suture bridge as used with a simple interrupted suture.

The disclosed suture bridges will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various suture bridges are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to given example will be described in that particular example. The reader should understand that a given feature need not be the same or similar to the specific portrayal of a related feature in any given figure or example.

With reference to FIGS. 1-4, a first example of a suture bridge, suture bridge 100, will now be described. Suture bridge 100 includes a first leg 106, a second leg 108, a first support 110, a second support 112, and a traversing member 114. Suture bridge 100 also includes a bottom surface 102 and a top surface 104 opposite of bottom surface 102. Suture bridge 100 functions to extend the useful life of sutures and to reduce damage to skin while being employed by the most common suture patterns.

Suture bridge 100 addresses many of the shortcomings existing with current suture techniques and devices. For example, suture bridge 100 extends the useful life of sutures. By elevating the sutures away from a patient's skin, the suture will last longer without causing irritation to the skin. Additionally, because pressure from the suture is reduced and more evenly spread across the surface of a patient's skin, a suture can stay in longer, allowing a wound more time to heal while avoiding conditions such as necrosis of the skin.

Suture bridge 100 can also be employed by many common types of suture patterns, including a simple interrupted suture, horizontal mattress suture, and a vertical mattress suture. Suture bridge 100 is sturdy and rigid enough to not collapse under the forces of any common type of suture while still compressing the wound, encouraging wound eversion and proper healing of the wound.

As can be seen in FIGS. 1-4, there are at least two legs, where first leg 106 and second leg 108 are located at opposite ends of suture bridge 100. Located on bottom surface 102 of suture bridge 100 at first leg 106 and second leg 108 are patient contacting surfaces 126. Patient contacting surfaces 126 reduce the overall pressure on a patient's skin 136 that would normally occur without suture bridge 100, allowing for longer use of the suture. In alternate embodiments, there may be multiple legs and multiple patient contacting surfaces.

First leg 106 and second leg 108 are of a sufficient thickness to be sturdy, yet still flexible. Alternatively, a different and more flexible material could be used for the first leg and the second leg to allow for different degrees of flexibility in the legs.

The flexibility of first leg 106 and second leg 108 allows them to contort and adapt to a patient's skin 136 as the patient moves. The legs are flexible to reduce skin irritation and pressure necrosis and allow movement of the patient's skin. Additionally, the flexibility of first leg 106 and second leg 108 provides for better patient comfort and reduces annoyances, such as suture bridge 100 catching on articles of clothing.

First leg 106 and second leg 108 each contain a hole 120. Holes 120 on first leg 106 and second leg 108 extend fully through suture bridge 100 from top surface 104 to bottom surface 102. Holes 120 can be used with a simple interrupted suture to secure suture bridge 100 to a patient over a wound 138 to extend the life of the suture and to encourage proper healing of the wound. In alternate embodiments, holes 120 may be notches in first leg 106 and second leg 108.

Protruding from a side of second leg 108 is tab 122. In alternative embodiments, the tab can extend from another side of the second leg or from any side of the first leg. Tab 122 includes second hole 124 that extends fully through suture bridge 100 from top surface 104 to bottom surface 102. Second hole 124 on tab 122 can be used with a horizontal mattress suture to secure suture bridge 100 to a patient over a wound 138 to extend the life of the suture and encourage proper healing of the wound. In this example, second hole 124 is substantially similar in size and shape to holes 120. However, second hole 124 can be suitable size and shape to accommodate a suture and secure suture bridge 100 to a patient over a wound.

First leg 106 is connected to a first support 110, and second leg 108 is connected to a second support 112. First support 110 and second support 112 rise up and slope inwardly at an angle from first leg 106 and second leg 108. First support 110 and second support 112 may be thicker, as measured from top surface 104 to bottom surface 102, than first leg 106 and second leg 108. The thickness of first support 110 and second support 112 increase the stiffness of first support 110 and second support 112 as compared to first leg 106 and second leg 108. In alternate embodiments, first support 110 and second support 112 increase stiffness by incorporating alternate or additional materials. These materials may be incorporated by creating first support 110 and second support 112 entirely from different materials, or alternatively they may have and internal or external support structure.

At ends opposite first leg 106 and second leg 108, first support 110 and second support 112 are connected together by traversing member 114 at obtuse angles. Together, first leg 106, second leg 108, first support 110, second support 112, and traversing member 114 define a bridge structure. Traversing member 114 is located in between first leg 106 and second leg 108 and is elevated away from first leg 106 and second leg 108 by first support 110 and second support 112 to form an elevated wound eversion void 132.

Wound eversion void 132 is formed beneath traversing member 114 and is configured to accept an everting wound 138. Similar to first support 110 and second support 112, traversing member 114 is thicker, as measured from top surface 104 to bottom surface 102, than first leg 106 and second leg 108. The added thickness of traversing member 114, along with first support 110 and second support 112, provide a greater stiffness for suture bridge 100 in its elevated portion. The increased stiffness helps withstand forces of different suture patterns and helps resist suture bridge 100 collapsing or bending at wound eversion void 132. In alternate embodiments, first support 110 and second support 112 increase stiffness by incorporating alternate or additional materials, in addition to or instead of adjusting thickness.

As can be seen in FIGS. 1-4, traversing member 114 is elevated away from a patient's skin 136 and wound 138. Traversing member being elevated and rigid helps facilitate wound eversion into wound eversion void 132 as wound 138 is compressed together by suture bridge 100 and the accompanying suture. When suture bridge 100 is used with a suture on a wound, wound eversion void 132 is positioned generally above the wound to facilitate wound eversion. Wound 138 may or may not contact bottom surface 102 in wound eversion void 132.

First leg 106 and first support 110 connect to form an obtuse angle at inflection point 116. Likewise, second leg 108 and second support 112 connect to form an obtuse angle at inflection point 118. Inflection points 116 and 118 cradle and trap sutures, for example, horizontal mattress sutures, that are compressing downward and inward on suture bridge 100. In the present example, inflection points 116 and 118 are somewhat defined angles, as opposed to a smooth curve, to restrict inward movement of the suture. Inflection points 116 and 118 help enable common suture patterns, like a horizontal mattress suture, to be used with suture bridge 100.

Ridge 128 is located on top surface 104 of suture bridge 100 primarily along the length of traversing member 114. In some examples the ridge extends down the length of the first support and the second support 112. Ridge 128 provides added strength, rigidity, and stiffness to suture bridge 100 to help withstand inward and downward compressive forces applied by a suture. Additionally, ridge 128 forms a groove 130.

Figure 2:
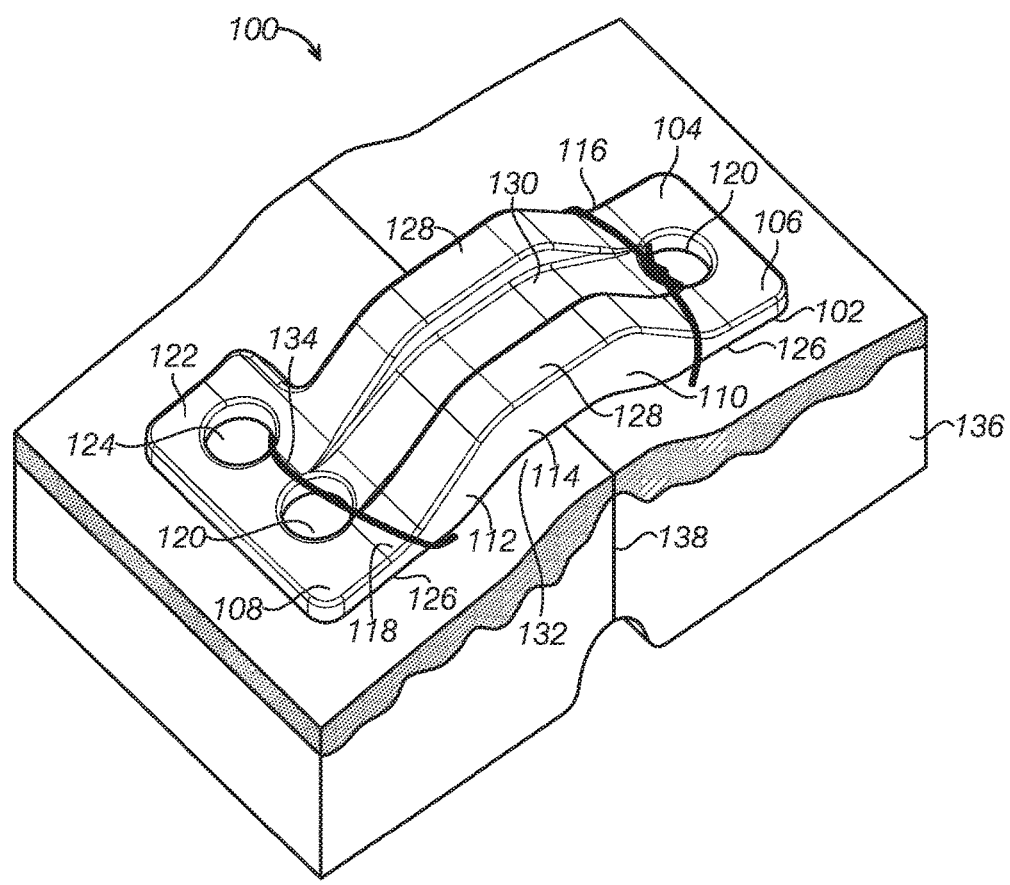
FIG. 2 is a perspective view of the suture bridge shown in FIG. 1 as used with a horizontal mattress suture.
Figure 3:
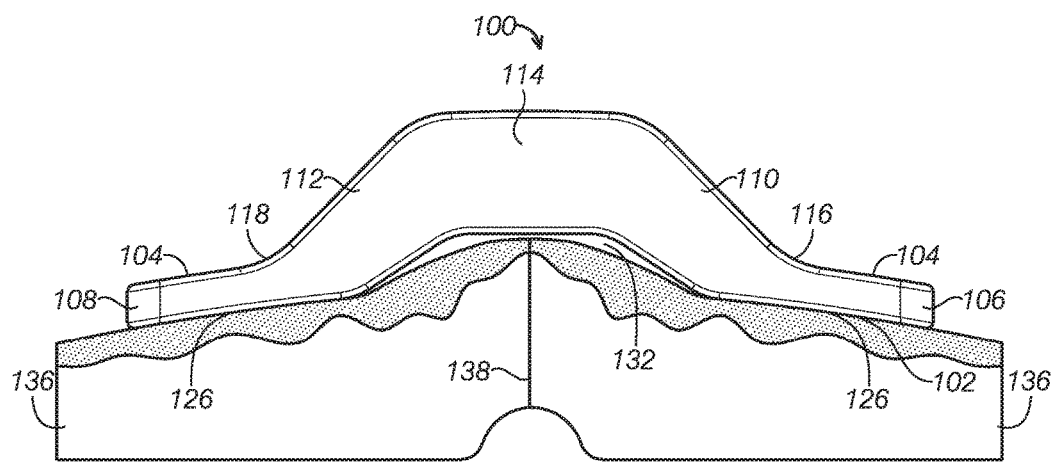
FIG. 3 is a front view of the suture bridge shown in FIG. 1 as used with a simple interrupted suture depicting a wound eversion extending into a wound eversion void.
Figure 4:
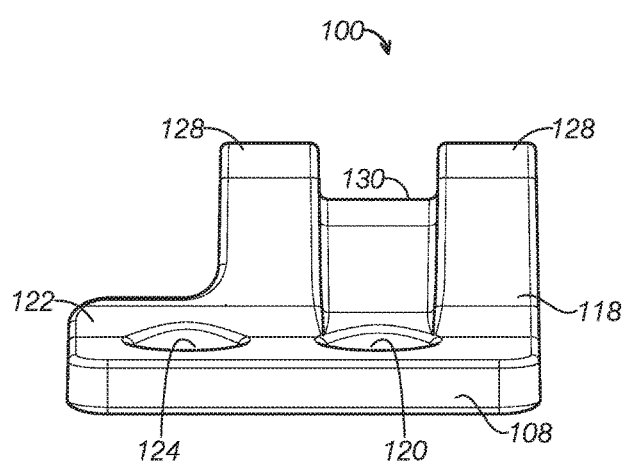
FIG. 4 is a side view of the suture bridge shown in FIG. 1 depicting a ridge and a groove.

As shown in FIGS. 1, 2, and 4, groove 130 is formed within ridge 128. Groove 130 extends parallel to ridge 128 along the length of traversing member 114 on top surface 104 of suture bridge 100. Groove 130 functions to hold a suture, such as a simple interrupted suture, within groove 130.

The suture bridge may be formed partially or entirely from any sturdy and resilient material, such as silicone, thermoplastic polyurethanes (TPU), rubber, metal, plastic, polypropylene, polyethlene, acrylonitrile butadiene styrene (ABS), high impact polystyrene (HIPS), poly vinyl chloride (PVC) polycarbonate, thermoplastic elastomers, polybutylene terephthalate, ethylene vinyl acetate, nylon a low-density polyethylene, linear low-density polyethylene, etc. The suture bridge may be made of one material of varying thickness, or by using a spine or ridge, to provide support for the traversing member while remaining flexible at the first leg and the second leg. Alternatively, the suture bridge may be made of one or more different materials to provide support and strength for the traversing member while remaining flexible at the first leg and the second leg. The materials may be incorporated creating the suture bridge, support structures, and legs from different materials, or alternatively they may have and internal or external support structures.

In some embodiments of the suture bridge, the entire suture bridge or a portion, for example, the bottom surface 102 may include a coating of additional medications. In these embodiments, a coating of one or a combination of growth factors, antimicrobials, or other agents for transfer to a patient's skin and wound to assist in proper healing of the wound. Alternatively, in some embodiments, the suture bridge may entirely or partially be impregnated with one or more additional medications to assist in proper healing of the wound.

With reference to FIG. 1, an example of how suture bridge 100 is used with a simple interrupted suture to close a wound is shown. Suture bridge 100 is positioned across wound 138 such that first leg 106 and second leg 108 are on opposite sides of wound 138, and wound eversion void 132 is above wound 138 to accommodate wound eversion. A suture thread 134 is inserted through hole 120 in first leg 106. The suture thread 134 is then stitched through or across wound 138 and is drawn out on the opposite side through hole 120 in second leg 108. Suture thread 134 is then pulled taught to close wound 138 and a knot tied, securing suture bridge 100, closing wound 138, and everting wound 138 into wound void 132.

Turning to FIG. 2, an example of how suture bridge 100 is used with a horizontal mattress suture to close a wound is shown. Suture bridge 100 is positioned across wound 138 such that first leg 106 and second leg 108 are on opposite sides of wound 138, and wound eversion void 132 is above wound 138 to accommodate wound eversion. A suture thread 134 is stitched through or across wound 138 and is drawn out on the opposite side.

Suture thread 134 is then threaded over second leg 108 and through hole 124 on tab 122. The suture thread 134 is then stitched back through or across wound 138 and is drawn out on the opposite side. The suture thread 134 is then threaded over first leg 106, pulled taught to close wound 138 and a knot tied, securing suture bridge 100, closing wound 138, and everting the wound into wound eversion void 132.

Figure 5:
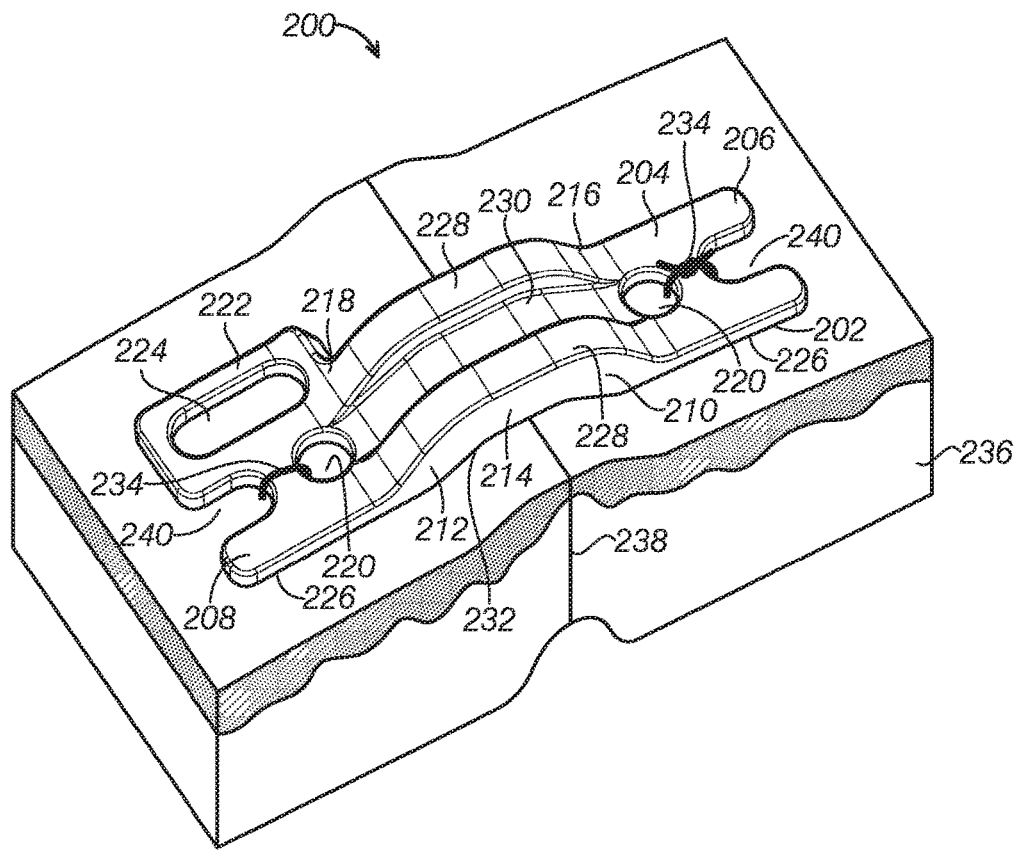
FIG. 5 is a perspective view of a second example of a suture bridge, the suture bridge including notches in opposite ends of the suture bridge to assist with a vertical mattress suture.
Figure 6:
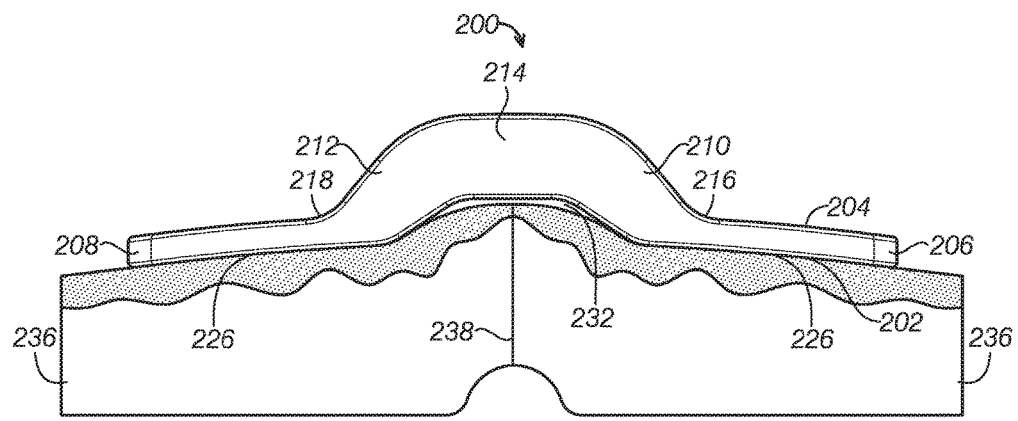
FIG. 6 is a front view of the suture bridge shown in FIG. 5 as used with a simple interrupted suture and depicting a wound eversion extending into a wound eversion void.
Figure 7:
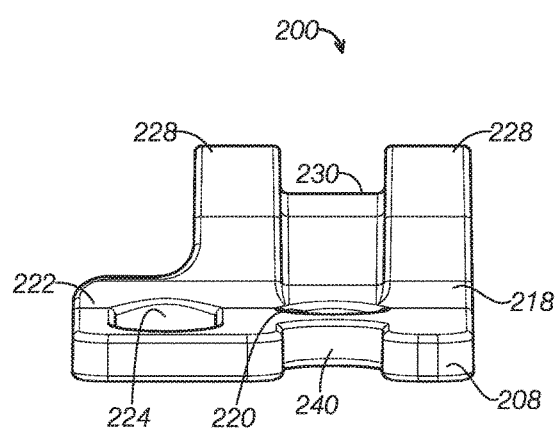
FIG. 7 is a side of the suture bridge shown in FIG. 5 depicting a ridge and a groove.

Turning now to FIGS. 5-7, a second example of a suture bridge, suture bridge 200, will now be described. Suture bridge 200 includes many similar or identical features to suture bridge 100. Thus, for the sake of brevity, each feature of suture bridge 200 will not be redundantly explained. Rather, key distinctions between suture bridge 100 and suture bridge 200 will be described in detail and the reader should reference the discussion above for features substantially similar between the two suture bridges.

With reference to FIGS. 5-7, suture bridge 200 includes a first leg 206, a second leg 208, a first support 210, a second support 212, and a traversing member 214. Suture bridge 200 also includes a bottom surface 202 and a top surface 204 opposite of bottom surface 202. Suture bridge 200 functions to extend the useful life of sutures and to reduce damage to skin while being employed by the most common suture patterns.

As can be seen in FIGS. 5-7, first leg 206 and second leg 208 are located at opposite ends of suture bridge 200. Located on bottom surface 202 of suture bridge 200 at first leg 206 and second leg 208 are patient contacting surfaces 226. First leg 206 and second leg 208 are of a sufficient thickness to be sturdy, yet flexible. Different materials can be used for the first leg and the second leg to allow for different degrees of flexibility in the legs. The flexibility of the legs allows for first leg 206 and second leg 208 to contort and adapt to a patient's skin 236 as the patent moves.

First leg 206 and second leg 208 each contain a hole 220. Holes 220 on first leg 206 and second leg 208 extend fully through suture bridge 200 from top surface 204 to bottom surface 202. Holes 220 can be used with a simple interrupted suture to secure suture bridge 100 to a patient over a wound to extend the life of the suture and encourage proper healing of the wound.

First leg 206 and second leg 208 each contain a notch 240 located next to holes 220 at opposite ends of suture bridge 200. Notches 240 on an end of first leg 206 and an end of second leg 208 extend fully through suture bridge 200 from top surface 204 to bottom surface 202. Notches 240 can be used with a vertical mattress suture to secure suture bridge 200 to a patient over a wound 238 to extend the life of the suture and encourage proper healing of the wound. In alternate embodiments, notches 240 may be holes located in first leg 206 and second leg 208 located next to holes 220.

As seen in FIGS. 5 and 7, tab 222 protrudes from a side of second leg 208. In alternative embodiments, the tab can extend from another side of the second leg or from any side of the first leg. Tab 222 includes second hole 224 that extends fully through suture bridge 200 from top surface 204 to bottom surface 202. Second hole 224 on tab 222 can be used with a horizontal mattress suture to secure suture bridge 200 to a patient over a wound 238 to extend the life of the suture and encourage proper healing of the wound. In this example, second hole 224 is substantially oval in shape. However, the second hole can be of any suitable size and shape to accommodate a suture and secure the suture bridge to a patient over a wound.

First leg 206 is connected to a first support 210, and second leg 208 is connected to a second support 212. First support 210 and second support 212 rise up and slope inwardly at an angle from first leg 206 and second leg 208. First support 210 and second support 212 are thicker, as measured from top surface 204 to bottom surface 202, than first leg 206 and second leg 208.

First support 210 and second support 212 are connected together by traversing member 214 at ends distal first leg 206 and second leg 208. Together, first leg 206, second leg 208, first support 210, second support 212, and traversing member 214 define a bridge structure. Traversing member 214 is located between first leg 206 and second leg 208 and elevated away from first leg 206 and second leg 208 to form an elevated wound eversion void 232.

As shown in FIGS. 5-7, traversing member 214 is elevated away from a patient's skin 236 and wound 238. Traversing member 214 being elevated and rigid facilitates wound eversion into wound eversion void 232 as wound 238 is compressed together by suture bridge 200 and the accompanying suture. When suture bridge 200 is used with a suture on a wound, wound eversion void 232 is positioned generally above the wound to facilitate wound eversion. Wound 238 may or may not contact bottom surface 202 in wound eversion void 232.

First leg 206 and first support 210 connect to form an obtuse angle at inflection point 216. Likewise, second leg 208 and second support 212 connect to form an obtuse angle at inflection point 218. Inflection points 216 and 218 cradle and trap sutures, specifically horizontal mattress sutures, that are compressing downward and inward on suture bridge 200.

Ridge 228 is located on top surface 204 of suture bridge 200 primarily along the length of traversing member 214. The ridge can additionally extend down the length of the first support and the second support. Ridge 228 provides added strength, rigidity, and stiffness to suture bridge 200 to withstand inward and downward compressive forces applied when used with a suture. Additional, ridge 228 forms a groove 230. Groove 230, extends parallel to ridge 228 along the length of traversing member 214 on top surface 204 of suture bridge 200.

The suture bridge contemplated in FIGS. 5-7 may be formed partially or entirely from any sturdy and resilient material, such as silicone, thermoplastic polyurethanes (TPU), rubber, polypropylene, polyethylene, acrylonitrile butadiene styrene (ABS), high impact polystyrene (HIPS), poly vinyl chloride (PVC) polycarbonate, thermoplastic elastomers, polybutylene terephthalate, ethylene vinyl acetate, nylon and low-density polyethylene, linear low-density polyethylene, etc. The suture bridge may be made of one material of varying thickness to provide support for the traversing member while remaining flexible at the first leg and the second leg. Alternatively, the suture bridge may be made of multiple different materials to provide support and strength for the traversing member while remaining flexible at the first leg and the second leg.

In some embodiments of the suture bridge, bottom surface 202 may include a coating of additional medications. In these embodiments, a coating of one or a combination of growth factors, antimicrobials, or other agents for transfer to a patient's skin and wound to assist in proper healing of the wound. Alternatively, in some embodiments, the suture bridge is impregnated with one or more additional medications to assist in proper healing of the wound.

Turning to FIG. 5, an example of how suture bridge 200 is used faith a vertical mattress suture to close a wound is shown. Suture bridge 200 is positioned across wound 238 such that first leg 206 and second leg 208 are on opposite sides of wound 238, and wound eversion void 232 is above wound 238 to accommodate wound eversion.

A suture thread 234 is threaded down through notch 240 on first leg 206 and stitched through or across wound 238 and is drawn out on the opposite side. Suture thread 234 is then threaded upward through notch 240 on second leg 208, over second leg 208, and down through hole 220 on second leg 208. Suture thread 234 is then stitched back through or across wound 238 and is drawn out on the opposite side. Suture thread 234 is then threaded up through hole 220 on first leg 206, over first leg 206, pulled taught to close wound 238 and a knot tied, securing suture bridge 200, closing wound 238, and everting wound 238 into wound eversion void 232.

The disclosure above encompasses multiple distinct inventions with independent utility. While each or these inventions has been disclosed in a particular form, the specific embodiments disclosed and illustrated above are not to be considerer in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims are to be considered within the subject matter of the inventions described herein.

The invention claimed is:

1. A system for wound closure, comprising:
   a suture bridge comprising:
      a first leg including a first patient contacting surface configured to contact a patient's skin, the first leg defining a first hole,
      a second leg spaced from the first leg and including a second patient contacting surface configured to contact the patient's skin, the second leg defining a second hole;

a first support connected to the first leg proximate the second leg, the first support and the first leg defining a first angle;

a second support connected to the second leg proximate the first leg, the second support and the second leg defining a second angle; and a traversing member extending between the first support and the second support, the traversing member being connected to the first support distal the first leg and connected to the second support distal the second leg, wherein the first support and the second support elevate the traversing member away from the first patient contacting surface of the first leg and from the second patient contacting surface of the second leg to define a wound eversion void below the traversing member for accepting an everting wound;

wherein the first leg, the first support, the traversing member, the second support and the second leg define a sidewall having varying thicknesses between a top surface and a bottom surface, a thickness of the sidewall being greatest at the traversing member and least at the first leg and the second leg; and wherein the first support and the second support have a first stiffness, and the first leg and the second leg have a second stiffness, the first stiffness being greater than the second stiffness; and a suture passing through the first hole of the first leg and the second hole of the second leg.

2. A system for wound closure, comprising:

a suture bridge comprising:

a first leg including a first patient contacting surface configured to contact a patient'skin, the first leg defining a first hole, a second leg spaced from the first leg and including a second patient contacting surface configured to contact the patient's skin, the second leg defining a second hole;

a first support connected to the first leg proximate the second leg, the first support and the first leg defining a first angle;

a second support connected to the second leg proximate the first leg, the second support and the second leg defining a second angle; and a traversing member extending between the first support and the second support, the traversing member being connected to the first support distal the first leg and connected to the second distal the second leg, wherein the first support and the second support elevate the traversing member away from the first patient contacting surface of the first leg and from the second patient contacting surface of the second leg to define a wound eversion void below the traversing member for accepting an everting wound; and wherein the first leg, the first support, the traversing member, the second support and the second leg define a sidewall having varying thickness between a top surface and a bottom surface, a thickness of the sidewall being greatest at the traversing member and least at the first leg and the second leg; and wherein the suture bridge includes elevated portions and skin-contacting portions, the elevated portions having greater stiffness than the skin-contacting portions; and a suture passing through the first hole of the first leg and the second hole of the second leg.

* * * * *